United States Patent
Drew

(10) Patent No.: US 10,092,721 B2
(45) Date of Patent: Oct. 9, 2018

(54) MULTI-LUMEN BREATHING CIRCUIT INCLUDING A FLEXIBLE PRINTED CIRCUIT BOARD ASSEMBLY

(71) Applicant: TELEFLEX MEDICAL INCORPORATED, Research Triangle Park, NC (US)

(72) Inventor: Douglas Roy Drew, Raleigh, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 288 days.

(21) Appl. No.: 14/776,217

(22) PCT Filed: Mar. 12, 2014

(86) PCT No.: PCT/US2014/024449
§ 371 (c)(1),
(2) Date: Sep. 14, 2015

(87) PCT Pub. No.: WO2014/165116
PCT Pub. Date: Oct. 9, 2014

(65) Prior Publication Data
US 2016/0001032 A1 Jan. 7, 2016

Related U.S. Application Data

(60) Provisional application No. 61/779,645, filed on Mar. 13, 2013.

(51) Int. Cl.
*A61M 16/00* (2006.01)
*A61M 16/10* (2006.01)
(Continued)

(52) U.S. Cl.
CPC .... *A61M 16/1095* (2014.02); *A61M 16/0875* (2013.01); *A61M 16/0883* (2014.02);
(Continued)

(58) Field of Classification Search
CPC .......... A61M 16/1095; A61M 16/0883; A61M 16/0875; A61M 2205/583; A61M 2205/3592; A61M 2205/3673; A61M 16/161; A61M 2205/587; A61M 2205/50; A61M 2205/3368
See application file for complete search history.

(56) References Cited

U.S. PATENT DOCUMENTS 6,167,883 B1   1/2001   Beran et al.
6,308,706 B1   10/2001  Lammers et al.
(Continued)

FOREIGN PATENT DOCUMENTS

WO      8401704  A1   5/1984

*Primary Examiner* — Steven Douglas
(74) *Attorney, Agent, or Firm* — Baker Hostetler LLP

(57) ABSTRACT

A breathing circuit includes a flexible hollow tube having a generally circular cross section and a flexible printed circuit board assembly disposed in the flexible hollow tube. The flexible printed circuit board assembly defines part of at least one inspiratory passage within the flexible hollow tube and part of at least one expiratory passage within the flexible hollow tube. The flexible printed circuit board assembly is configured to heat airflow within one or more of the at least one inspiratory passage and the at least one expiratory passage, and monitor a first property of the airflow within one or more of the at least one inspiratory passage and the at least one expiratory passage at multiple locations along the axial length of the flexible hollow tube.

15 Claims, 3 Drawing Sheets

(51) Int. Cl.
*A61M 16/08* (2006.01)
*A61M 16/16* (2006.01)

(52) U.S. Cl.
CPC ... *A61M 16/161* (2014.02); *A61M 2016/0027* (2013.01); *A61M 2016/0036* (2013.01); *A61M 2205/3368* (2013.01); *A61M 2205/3592* (2013.01); *A61M 2205/3673* (2013.01); *A61M 2205/50* (2013.01); *A61M 2205/583* (2013.01); *A61M 2205/587* (2013.01); *A61M 2230/43* (2013.01)

(56) References Cited

U.S. PATENT DOCUMENTS

| | | | | |
|---|---|---|---|---|
| 6,523,538 B1 * | 2/2003 | Wikefeldt | ............. | A61M 16/01 128/204.18 |
| 6,536,428 B1 * | 3/2003 | Smith | ................... | A61M 16/08 128/203.17 |
| 6,769,431 B2 * | 8/2004 | Smith | ................... | A61M 16/08 128/203.12 |
| 6,874,500 B2 * | 4/2005 | Fukunaga | ............. | A61M 16/00 128/203.12 |
| 8,371,300 B2 * | 2/2013 | Rapoport | ........... | A61M 16/0875 128/204.18 |
| 2004/0250815 A1 * | 12/2004 | Scott | ..................... | A61M 16/08 128/204.17 |
| 2005/0061321 A1 | 3/2005 | Jones | | |
| 2005/0223795 A1 | 10/2005 | Gerder et al. | | |
| 2006/0025700 A1 | 2/2006 | Fallik | | |
| 2008/0066748 A1 | 3/2008 | Felske et al. | | |
| 2008/0105257 A1 | 5/2008 | Klasek et al. | | |
| 2015/0165146 A1 * | 6/2015 | Bowman | ............ | A61M 16/0069 128/203.14 |

\* cited by examiner

MULTI-LUMEN BREATHING CIRCUIT INCLUDING A FLEXIBLE PRINTED CIRCUIT BOARD ASSEMBLY

CROSS REFERENCE TO RELATED APPLICATION

This application claims the benefit of U.S. Provisional Application No. 61/779,645, filed on Mar. 13, 2013, the disclosure of which is hereby incorporated by reference in its entirety.

FIELD OF THE INVENTION

This disclosure generally relates to controlling the temperature and/or humidity of airflow, and monitoring airflow properties in a multi-lumen breathing circuit configured to communicate a gas to a patient. More particularly, this disclosure relates to a multi-lumen breathing circuit including a flexible printed circuit board assembly that has integrated sensors, instruments, and/or indicators configured to heat the airflow and monitor the airflow properties at various locations within the multi-lumen breathing circuit.

BACKGROUND OF THE INVENTION

To assist medical patients having difficulty breathing, gases are supplied to and returned from the patients through multi-lumen breathing circuits. Because the gases are typically humidified and because of the difference between the atmospheric temperature and the temperature of the patient's breath, condensation commonly builds on the inside wall of the breathing circuits during use.

Various approaches have been implemented to reduce the condensation build up within the breathing circuits. In some known breathing circuits, collection points are provided within the breathing circuit tube for draining condensed liquid. In other known breathing circuits, a heating wire is included within the breathing circuit tube for maintaining or elevating the temperature of airflow or the temperature of the outer wall of the breathing circuit tube to reduce the formation of condensation. However, such heating wires may lead to ignition and subsequent fire, require their own power source, and are energy inefficient.

Currently, properties of the airflow in the multi-lumen breathing circuits are monitored by devices connected to the breathing circuits. For example, sensors can be included in ventilators connected to the proximal end of the breathing circuit tubes to monitor, for example, the temperature, rate, and/or gas content of the airflow. However, such measurements may not be accurate as the properties of the airflow may change along the axial length of the multi-lumen breathing circuits. For example, the temperature and rate of the airflow near the distal end of the multi-lumen breathing circuit in communication with the patient may differ from the temperature and rate of the airflow near the proximal end of the multi-lumen breathing circuit in communication with the measuring device. The inaccurate measurements may lead to lower quality care of the patients.

Therefore, a need exists to more effectively control the temperature and/or humidity of airflow, and monitor airflow properties at various points within a multi-lumen breathing circuit.

SUMMARY OF THE INVENTION

The foregoing needs are met, to a great extent, by implementations of the multi-lumen breathing circuit including a flexible printed circuit board assembly for controlling the temperature and/or humidity of airflow and monitoring airflow properties at various points within the multi-lumen breathing circuit.

In accordance with one implementation, a breathing circuit includes a flexible hollow tube having a generally circular cross section and a flexible printed circuit board assembly disposed in the flexible hollow tube. The flexible printed circuit board assembly defines part of at least one inspiratory passage within the flexible hollow tube and part of at least one expiratory passage within the flexible hollow tube. The flexible printed circuit board assembly is configured to heat airflow within one or more of the at least one inspiratory passage and the at least one expiratory passage, and monitor a first property of the airflow within one or more of the at least one inspiratory passage and the at least one expiratory passage at multiple locations along the axial length of the flexible hollow tube.

In some implementations, the flexible printed circuit board assembly can be disposed between an entirety of the axial length of the flexible hollow tube. The flexible printed circuit board assembly can be flat and have a dimension equal to the inner diameter of the flexible hollow tube. The flexible printed circuit board assembly can be disposed between two adjacent protrusions extending radially inward from an inner wall of the flexible hollow tube. The flexible printed circuit board assembly can define part of one inspiratory passage within the flexible hollow tube and part of one expiratory passage within the flexible hollow tube. The one inspiratory passage and the one expiratory passage can be defined at opposite sides of the flexible printed circuit board assembly.

In some implementations, the flexible printed circuit board assembly can have a generally circular cross section. The flexible printed circuit board assembly can be coaxial to the flexible hollow tube and can share a center axis with the flexible hollow tube. The flexible printed circuit board assembly can define part of one inspiratory passage within the flexible hollow tube and part of two or more expiratory passages within the flexible hollow tube.

In some implementations, the flexible hollow tube can be made of a material that is at least partially transparent. The flexible printed circuit board assembly can include one or more light emitting diodes that are configured to emit light if a predetermined condition of a monitored property of the airflow is detected. The flexible printed circuit board assembly can be permanently fixed in the flexible hollow tube.

In some implementations, the flexible printed circuit board assembly can be configured to monitor a first property of the airflow within the at least one inspiratory passage and a second property of the airflow within the at least one expiratory passage. The first property of the airflow within the at least one inspiratory passage and the second property of the airflow within the at least one expiratory passage can be the same type of property or different types of properties.

In some implementations, the first property can be temperature, humidity, pressure, airflow rate, presence of microbes or viruses, or concentration of a particular gas. The flexible printed circuit board assembly can include an integrated power and signal connector and can include a wireless communications circuit to transmit values for the monitored first property. The flexible printed circuit board assembly can include sensors that are uniformly or nonuniformly spaced apart along the axial length of the flexible hollow tube.

Certain implementations of the multi-lumen breathing circuit including the flexible printed circuit board assembly have been outlined so that the detailed description below may be better understood. There are, of course, additional implementations that will be described below and which will form the subject matter of the claims.

In this respect, before explaining at least one implementation in detail, it is to be understood that the multi-lumen breathing circuit including the flexible printed circuit board assembly is not limited in its application to the details of construction and to the arrangements of the components set forth in the following description or illustrated in the drawings. Also, it is to be understood that the phraseology and terminology employed herein, as well as in the Abstract, are for the purpose of description and should not be regarded as limiting.

As such, those skilled in the art will appreciate that the conception upon which this disclosure is based may readily be utilized as a basis for the designing of other structures, methods, and systems for carrying out the several purposes of the multi-lumen breathing circuit including the flexible printed circuit board assembly. It is understood, therefore, that the claims include such equivalent constructions insofar as they do not depart from the spirit and scope of the present application.

DETAILED DESCRIPTION

Figure 1:
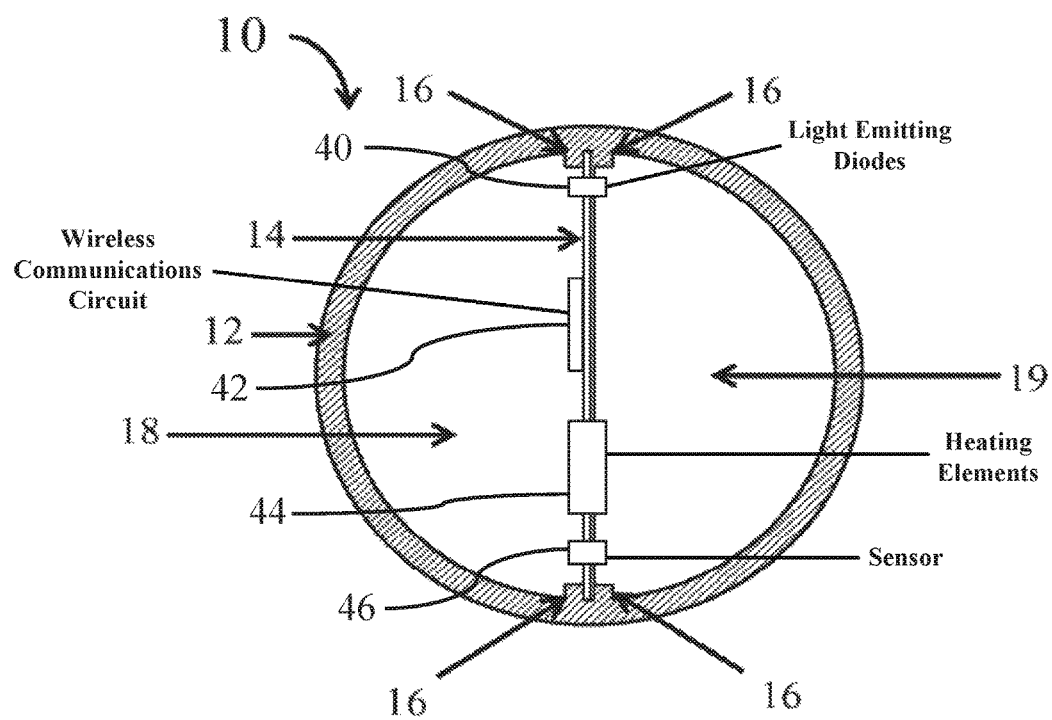
FIG. 1 is a cross-sectional view illustrating a first exemplary multi-lumen breathing circuit including the flexible printed circuit board assembly.

Implementations of the multi-lumen breathing circuit including the flexible printed circuit board assembly are described with reference to the drawings, in which like reference numerals refer to like parts throughout.

Referring to FIG. 1, a cross-sectional view of a first implementation of a multi-lumen breathing circuit 10 including the flexible printed circuit board assembly 14 is illustrated. The cross section of FIG. 1 is taken along a plane perpendicular to the central, longitudinal axis of a flexible hollow tube 12. The multi-lumen breathing circuit 10 includes the flexible hollow tube 12 having a generally circular cross section, protrusions 16 extending radially inward from an inner wall of the flexible hollow tube 12, and the flexible printed circuit board assembly 14. The two pairs of protrusions 16 are located at opposite sides of the flexible hollow tube 12. A gap is defined between each pair of protrusions 16 to receive and hold the flexible printed circuit board assembly 14. The thickness of the gap can be approximately equal to the thickness of the flexible printed circuit board assembly 14 so that the flexible printed circuit board assembly 14 is held by a friction fit between the pair of protrusions 16.

In some implementations, the flexible printed circuit board assembly 14 can be removably held by the protrusions 16 while in other implementations, the flexible printed circuit board assembly 14 can be permanently held by the protrusions 16 through use of an adhesive, chemical fusion, heat fusion, or the like. In some implementations, the flexible hollow tube 12 and the flexible printed circuit board assembly 14 can be manufactured simultaneously, while in other implementations, the flexible printed circuit board assembly 14 can be inserted into the flexible hollow tube 12 after the flexible hollow tube 12 has been manufactured.

An inspiratory passage 18 is defined by half of the circumference of the flexible hollow tube 12 and the flexible printed circuit board assembly 14. Therefore, the inspiratory passage 18 has a D-shaped cross section taken along the plane perpendicular to the central, longitudinal axis of the flexible hollow tube 12. An expiratory passage 19 is defined by the other half of the circumference of the flexible hollow tube 12 and the other side of the flexible printed circuit board assembly 14. Similarly, the expiratory passage 19 also has a D-shaped cross section taken along the plane perpendicular to and along the central, longitudinal axis of the flexible hollow tube 12.

In some implementations, as shown in FIG. 1, the location of the protrusions 16 and, thus, the flexible printed circuit board assembly 14 may be consistent along the inner circumference of the flexible hollow tube 12 throughout the axial length of the flexible hollow tube 12. In other implementations, however, the protrusions 16 may spiral along the inner circumference of the flexible hollow tube 12 throughout at least part of or an entirety of the axial length of the flexible hollow tube 12. As such, the flexible printed circuit board assembly 14 would also spiral along at least part of or the entirety of the axial length of the flexible hollow tube 12. A helical path for the airflow through the inspiratory passage 18 and the expiratory passage 19 would, therefore, be formed. The spiral configuration increases the length of the flexible printed circuit board assembly 14 within the flexible hollow tube 12, which increases the contact time of the airflow with the flexible printed circuit board assembly, thereby improving heat transfer to the airflow.

Figure 2:
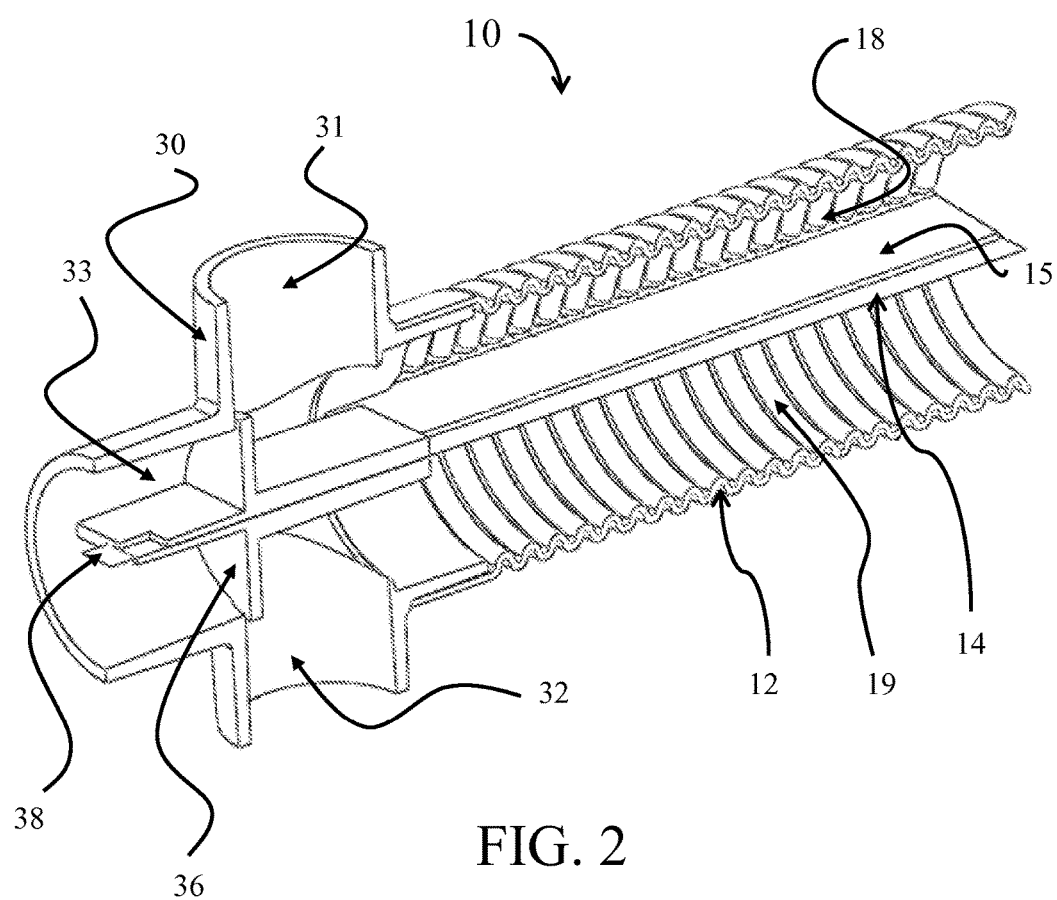
FIG. 2 is a cross-sectional perspective view of the proximal end of a flexible hollow tube of the first exemplary multi-lumen breathing circuit including the flexible printed circuit board assembly.

Referring to FIG. 2, a cross-sectional perspective view of the proximal end of the flexible hollow tube 12 of the first exemplary multi-lumen breathing circuit 10 including the flexible printed circuit board assembly is illustrated. The cross section of FIG. 2 is taken along a plane perpendicular to the flexible printed circuit board assembly 14 along its center, longitudinal axis. In the implementation shown in FIG. 2, the flexible printed circuit board assembly 14 extends partially along a wall 15 that extends along the diameter of the flexible hollow tube 12 to separate the inspiratory passage 18 and expiratory passage 19. For example, as shown in FIG. 2, the flexible printed circuit board assembly 14 extends along about the center third of the wall 15. In other implementations, the flexible printed circuit board assembly 14 can extend along the entire inner diameter of the flexible hollow tube 12.

At its proximal end, the flexible hollow tube 12 includes a connector shell 30. The connector shell 30 includes a inspiratory port 31, an expiratory port 32, and a power and signal port 33. Although the ports 31, 32, 33 have been shown as having circular cross sections, their cross section may take the form of any shape. For example, the ports 31, 32, 33 can have cross sections that are square, rectangular, pentagonal, hexagonal, or the like. The inspiratory port 31 can connect to a gas source, such as an oxygen source, a medicament source, or the like, to deliver the gas to the patient. The expiratory port 32 can connect to a ventilation device and/or be connected to an exhaust filter. The power and signal port 33 can connect to a device, such as the ventilation device, that receives the one or more properties of the airflow within one or more of the inspiratory passage 18 and the expiratory passage 19 at multiple locations along the axial, i.e., longitudinal, length of the flexible hollow tube 12. The device can also provide signals to control heating of the elements in the flexible printed circuit board assembly 14. In addition, the device can also provide power to the flexible printed circuit board assembly 14.

To separate the inspiratory passage 18 from the expiratory passage 19, as well as close the proximal end of the flexible hollow tube 12, an over-molded connector 36 is provided within the connector shell 30. In some implementations, the over-molded connector 36 can have dimensions slightly larger than the interior dimensions of the connector shell 30, so that the over-molded connector 36 is held in the connector shell 30 by a friction fit. In other implementations, the over-molded connector 36 can be permanently held in the connector shell 30 by use of an adhesive, chemical fusion, heat fusion, or the like.

A exposed part 38 of the flexible printed circuit board assembly 14 may be exposed at the proximal end of the over-molded connector 36. In some implementations, as shown in FIG. 2, the exposed part 38 can be within a cutout at the proximal end of the over-molded connector 36, whereas in other implementations, the exposed part 38 of the flexible printed circuit board assembly 14 can extend beyond the proximal end of the over-molded connector 36. The exposed part 38 is electrically connected to the device, such as the ventilation device to enable electrical communication between the flexible printed circuit board assembly 14 and the device.

Figure 3:
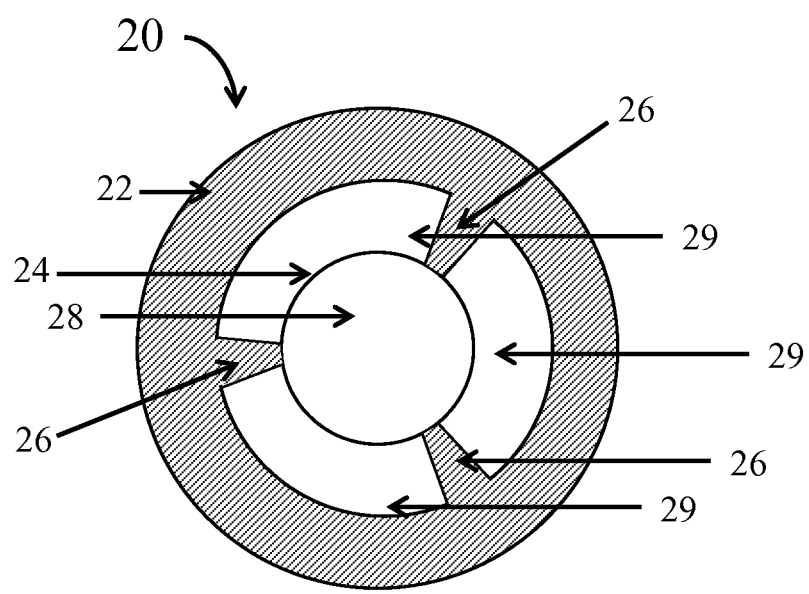
FIG. 3 is a cross-sectional view illustrating a second exemplary multi-lumen breathing circuit including the flexible printed circuit board assembly.

Referring to FIG. 3, a cross-sectional view of a second implementation of a multi-lumen breathing circuit 20 including the flexible printed circuit board assembly 24 is illustrated. The cross section of FIG. 3 is taken along the same plane of FIG. 1. In particular, cross section of FIG. 3 is taken along a plane perpendicular to the central, longitudinal axis of the flexible hollow tube 22. The multi-lumen breathing circuit 20 includes a flexible hollow tube 22 having a generally circular cross section, protrusions 26 extending radially inward from an inner wall of the flexible hollow tube 22, and the flexible printed circuit board assembly 24. The flexible printed circuit board assembly 24 also has a generally circular cross section. Three protrusions 26 are located circumferentially around the flexible printed circuit board assembly 24. Although three protrusions 26 are illustrated in FIG. 3, the flexible hollow tube 22 can include any number of protrusions 26 depending on the desired number of expiratory passages 29. For example, if two expiratory passages 29 are desired, then two protrusions 26 can be included in the flexible hollow tube 22 and if four expiratory passages 28 are desired, then four protrusions 26 can be included in the flexible hollow tube 22.

In some implementations, the flexible printed circuit board assembly 24 can be removably held by the protrusions 26 using, for example, textured surfaces, while in other implementations, the flexible printed circuit board assembly 24 can be permanently held by the protrusions 26 through use of an adhesive, chemical fusion, heat fusion, or the like. In some implementations, the flexible hollow tube 22 and the flexible printed circuit board assembly 24 can be manufactured simultaneously, while in other implementations, the flexible printed circuit board assembly 24 can be inserted into the flexible hollow tube 22 after the flexible hollow tube 22 has been manufactured.

An inspiratory passage 28 is completely defined by the circumference of the flexible printed circuit board assembly 24. Therefore, the inspiratory passage 28 has a generally circular cross section taken along the plane perpendicular to the central, longitudinal axis of the flexible hollow tube 22. The expiratory passages 29 are defined by the flexible printed circuit board assembly 24, the protrusions 26, and the inner wall of the flexible hollow tube 22.

In some implementations, as shown in FIG. 3, the flexible printed circuit board assembly 24 can be rolled about its central, longitudinal axis and the two ends of the flexible printed circuit board assembly 24 can be fixed to create the longitudinal, straight seam of the flexible printed circuit board assembly 24. In other implementations, the flexible printed circuit board assembly 24 can be twisted into a spiral configuration with the two ends of the flexible printed circuit board assembly 24 being fixed to create the generally circular cross section of the flexible printed circuit board assembly 24. A spiral tubular flexible printed circuit board assembly 24 may have a lower manufacturing cost and may increase heat transfer to the airflow in the inspiratory passage 28 and the expiratory passages 29 relative to the flexible printed circuit board assembly 24 formed as lengthwise, straight seam. The increased heat transfer of the spiral tubular flexible printed circuit board assembly 24 may be due to an increased density of heating elements along the axial length of the flexible hollow tube 22 because of the spiraling.

In some implementations, the flexible hollow tube 22 may not include the protrusions 26, such that the flexible printed circuit board assembly 24 is free to move within the flexible hollow tube 22. In such implementations, a single inspiratory passage 28 is completely defined by the circumference of the flexible printed circuit board assembly 24 and a single expiratory passage 29 is defined between the inner wall of the flexible hollow tube 22 and the outer wall of the flexible printed circuit board assembly 24.

The distal end of the flexible hollow tube 12, 22 can be in communication with a patient through, for example, a mouthpiece, a breathing mask, or the like. As described above, at the proximal end of the flexible hollow tube 12, 22, the inspiratory passage 18, 28 can be connected to a gas source, such as an oxygen source, a medicament source, or the like, through the inspiratory port 31, to deliver the gas to the patient. Further, at the proximal end of the flexible hollow tube 12, 22, the expiratory passages 19, 29 can terminate in the expiratory port 32, to be connected to a ventilation device, and/or be connected to an exhaust filter.

In some implementations, the flexible printed circuit board assembly 14, 24 can extend along an entirety of the axial length of the flexible hollow tube 12, 22. In other implementations, the flexible printed circuit board assembly 14, 24 can partly extend along the axial length of the flexible hollow tube 12, 22. To maintain the separation between the inspiratory passage 18, 28 and the expiratory passages 19, 29, in such implementations, a flexible sheet or tube can be fixed where the flexible printed circuit board assembly 14, 24 does not extend.

In some implementations, the flexible hollow tube 12, 22 can be corrugated and made from a flexible a plastic, such as polyethylene or another material suitable for carrying gas with relatively high humidity. In some implementations where a visible gas is communicated to a patient or visual indicators, such as light emitting diodes 40 (an embodiment of which are depicted schematically in FIG. 1), are included on the flexible printed circuit board assembly 14, 24, the flexible hollow tube 12, 22 may be at least partially transparent to allow visual inspection within the flexible hollow tube 12, 22.

The flexible printed circuit board assembly 14, 24 includes a flexible polymer substrate, such as a flexible plastic substrate made of polyimide, polyether ether ketone, transparent conductive polyester, or the like. One or more conductive layers including the heating elements, sensors, instruments, and/or indicators are formed on one or both sides of the flexible polymer substrate. In some implementations, the flexible printed circuit board assembly 14, 24 can be single-sided such that only one side of the flexible printed circuit board assembly 14, 24 has a single conductor layer made of, for example, a metal or conductive polymer. In such implementations, the functionalities of the flexible printed circuit board assembly 14, 24 may be applicable to either one of the inspiratory passage 18, 28 or the expiratory passages 19, 29.

In other implementations, the flexible printed circuit board assembly 14, 24 can be double-sided such that both sides of the flexible printed circuit board assembly 14, 24 have conductor layers made of, for example, a metal or conductive polymer. In such implementations, the functionalities of the flexible printed circuit board assembly 14, 24 may be applicable to both the inspiratory passage 18, 28 and the expiratory passages 19, 29.

The flexible printed circuit board assembly 14, 24 can be fabricated with or without a protective coating on its conductive layer(s). In preferred implementations, because the airflow in the flexible hollow tube 12, 22 is relatively humid, the conductive layer(s) of the flexible printed circuit board assembly 14, 24 can be covered with a protective coating to avoid failure due, for example, to short-circuiting.

The flexible printed circuit board assembly 14, 24 can include an integrated power and signal connector, such as the exposed part 38, at the proximal end of the flexible hollow tube 12, 22. The integrated power and signal connector can be configured to be connected to, for example, a ventilator device to provide power to the flexible printed circuit board assembly 14, 24, transmit signals indicative of the measurements of the monitored properties of the airflow from the flexible printed circuit board assembly 14, 24, and receive signals to activate or deactivate particular functionalities of the flexible printed circuit board assembly 14, 24. The signals can be received or transmitted in series or in parallel.

In some implementations, a wireless communications circuit 42 (an embodiment of which is depicted schematically in FIG. 1) may be included in the flexible printed circuit board assembly 14, 24, such that the integrated power and signal connector may only be an integrated power connector. The wireless communications circuit 42 can enable a medical practitioner to verify that the multi-lumen breathing circuit 10, 20 is powered and properly functioning from a remote location. Moreover, the wireless communications circuit 42 can enable remote, automated monitoring of patients.

In some implementations, a wireless power circuit may be included in the flexible printed circuit board assembly 14, 24, such that the integrated power and signal connector may not be included at the proximal end of the flexible hollow tube 12, 22. The wireless power circuit can be configured to receive energy by electromagnetic induction, electromagnetic radiation, and/or electrical conduction.

The flexible printed circuit board assembly 14, 24 is configured to perform multiple functions. First, the flexible printed circuit board assembly 14, 24 can be configured to heat the airflow in one or more of the inspiratory passage 18, 28 and the expiratory passages 19, 29 to reduce the condensation in the flexible hollow tube 12, 22. The flexible printed circuit board assembly 14, 24 can include heating elements 44 (an embodiment of which is depicted schematically in FIG. 1), such as coils, to heat the air flow. The heating elements 44 can be included at predetermined points along the axial length flexible printed circuit board assembly 14, 24 that are or are not uniformly separated. For example, the heating elements 44 may be further spaced apart at the proximal and distal ends of the flexible hollow tube 12, 22 than in the middle regions of the flexible hollow tube 12, 22 and vice versa.

Relative to the current heating wires included in breathing circuits, the flexible printed circuit board assembly 14, 24 has a significantly greater effective surface area, thereby reducing the likelihood of ignition or fire due to overheating of a region of the flexible hollow tube 12, 22, increasing heat transfer rates, and improving energy efficiency.

In addition, the flexible printed circuit board assembly 14, 24 can be configured to monitor one or more properties of airflow within one or more of the inspiratory passage 18, 28 and the expiratory passages 19, 29 at multiple locations along the axial length of the flexible hollow tube 12, 22. The one or more monitored properties can be one or more of temperature, humidity, pressure, airflow rate, presence of microbes or viruses, and concentration of a particular gas. As such, to monitor the properties of airflow, the flexible printed circuit board assembly 14, 24 can include at least one sensor 46 (an embodiment of which is depicted schematically in FIG. 1), which may include temperature sensors, instruments, and/or indicators; absolute or relative humidity sensors, instruments, and/or indicators; pressure sensors, instruments, and/or indicators; airflow rate sensors, instruments, and/or indicators; medical "lab-on-chip" sensors, instruments, and/or indicators; visual indicators such as light emitting diodes 40; wireless communications devices; and integrated power and signal connectors.

In some implementations, the various sensors, instruments, and/or indicators can be integral with the substrate of the flexible printed circuit board assembly 14, 24. The various sensors, instruments, and/or indicators can be included at predetermined points along the axial length flexible printed circuit board assembly 14, 24 that are or are not uniformly separated. For example, the various sensors, instruments, and/or indicators may be further spaced apart at the proximal and distal ends of the flexible hollow tube 12, 22 than in the middle regions of the flexible hollow tube 12, 22 and vice versa.

In some implementations, the medical "lab-on-chip" sensors integrated on the flexible printed circuit board assembly 14, 24 are configured to detect airborne microbes or viruses exhaled by the patient or within the inspiratory passage 18, 28. Moreover, these sensors can be configured to monitor the concentration of particular gases in the inspiratory passage 18, 28 or expiratory passage 19, 29. For example, the concentration of medicaments, oxygen, carbon dioxide, or the like can be monitored by the medical "lab-on-chip" sensors.

In some implementations, visual indicators, such as light emitting diodes 40, are included on the flexible printed circuit board assembly 14, 24. These visual indicators can be configured to emit light if a predetermined condition is met. In one implementation, the visual indicators can emit light if the multi-lumen breathing circuit 10, 20 is powered to enable medical practitioners and/or patients to know whether the multi-lumen breathing circuit 10, 20 is functioning from a distance. In another implementation, the visual indicators can emit light or change the color or pattern of the emitted light if a monitored property falls below or rises above a predetermined threshold. For example, if the temperature of the airflow within the flexible hollow tube 12, 22 increases above a predetermined threshold, the visual indicators can emit light, change the color of the emitted light to, for example, red, or emit light according to, for example, a blinking pattern to inform the medical practitioner and/or patient. In yet another implementation, the visual indicators can be configured to display a value of a monitored property. For example, the value of the temperature can be displayed by the visual indicators at one or more locations along the axial length of the flexible hollow tube 12, 22. In still another implementation, the visual indicators can emit light or change the color or pattern of the emitted light if the multi-lumen breathing circuit 10, 20 has exceeded its useful operating time or useful shelf time. For example, a constant red color can be emitted by the visual indicators if the useful operating or shelf time of the multi-lumen breathing circuit 10, 20 has been exceeded.

In some implementations, in addition to visually indicating that the useful operating or shelf time of the multi-lumen breathing circuit 10, 20 has been exceeded, the flexible printed circuit board assembly 14, 24 can also be configured to no longer operate if the useful operating or shelf time of the multi-lumen breathing circuit 10, 20 has been exceeded.

The accuracy and response time of the various sensors are improved relative to current sensors used in breathing circuits because of the reduced thermal mass of the sensors and the direct exposure of the sensors to the airflow. More accurate and rapid feedback from the various sensors at various locations within the flexible hollow tube 12, 22 permits a greater ability to control the airflow. The sensor feedback may be used for open-loop or closed-loop control of the parameters of the airflow, such as temperature, humidity, pressure, airflow rate, and concentration of particular gases or medicaments.

Because the various sensors, instruments, and/or indicators are included on the same flexible printed circuit board assembly 14, 24 with the heating elements, only a single power connection and a single signal connector may be connected to the multi-lumen breathing circuit 10, 20. This reduces the time and efforts required by a medical practitioner to setup or disconnect the multi-lumen breathing circuit 10, 20. Moreover, fewer external wires reduce the likelihood that a patient removes one or more of the sensors, reduce the likelihood of inadvertent snagging, kinking, breaking, or tangling of the external wires, result in a cleaner appearance, and reduce the surface areas required for cleaning.

In addition, as opposed to current breathing circuits, the multi-lumen breathing circuit 10, 20 does not need to be broken to add or delete various sensors. Rather, the various sensors can be activated or deactivated electronically. By not breaking the multi-lumen breathing circuit 10, 20, the likelihood of ventilator-associated pneumonia, the risk of exposure of the patient to environmental microbial contamination, and the risk of exposure of the medical practitioner to microbial contamination from the patient are reduced.

Reusable or disposable sensors of the types described above or of other types can be connected to the flexible printed circuit board assembly 14, 24. As such, the reusable or disposable sensors can be powered and send data through the flexible printed circuit board assembly 14, 24. The reusable sensors may be inserted into the multi-lumen breathing circuit 10, 20 through the wall of the flexible hollow tube 12, 22.

The flexible printed circuit board assembly 14, 24 may be disposable, which eliminates cleaning, sterilization, and replacement of the various sensors, instruments, and/or indicators on the flexible printed circuit board assembly 14, 24.

Testing of the multi-lumen breathing circuit 10, 20 including the flexible printed circuit board assembly 14, 24 has shown that surface temperatures of over 200° C. (390° F.) may be achieved on the flexible printed circuit board assembly 14, 24 without combustion of the flexible hollow tube 12, 22 or other physical degradation. The flexible printed circuit board assembly 14, 24 requires a low power of about 30 watts and about 3.2 amperes relative to current heating wires to operate. As such, a smaller power supply can be connected to the multi-lumen breathing circuit 10, 20, which reduces the cost and maintenance of the multi-lumen breathing circuit 10, 20. Temperature sensors, such as 10 kΩ thermistors, integrated into the flexible printed circuit board assembly 14, 24 were tested to have an accuracy of about 99%.

The many features and advantages of the multi-lumen breathing circuit 10, 20 including the flexible printed circuit board assembly 14, 24 are apparent from the detailed specification, and thus, the claims cover all such features and advantages within the scope of this application. Further, numerous modifications and variations are possible.

For example, the design of the flexible printed circuit board assembly 14, 24 can be changed without changing the method of manufacture or the manufacturing hardware of the multi-lumen breathing circuit 10, 20. For example, functionalities of the flexible printed circuit board assembly 14, 24 can be added or removed by changing the circuit designs of the flexible printed circuit board assembly 14, 24. Moreover, in implementations where the flexible printed circuit board assembly 14, 24 is releasably connected to the flexible hollow tube 12, 22, the flexible printed circuit board assembly 14, 24 can be replaced with an updated flexible printed circuit board assembly 14, 24.

The flexible printed circuit board assembly 14, 24 can be used in any airflow circuit. For example, the flexible printed circuit board assembly 14, 24 can be implemented in continuous positive airway pressure devices, endotracheal tubes, pressurized endoscopes, airflow tubes for surgical applications, and non-medical, e.g., industrial, airflow tubes.

As such, it is not desired to limit the multi-lumen breathing circuit 10, 20 including the flexible printed circuit board assembly 14, 24 to the exact construction and operation described and illustrated, and accordingly, all suitable modifications and equivalents may fall within the scope of the claims.

What is claimed is:
1. A breathing circuit, comprising:
a flexible hollow tube having a generally circular cross section, the flexible hollow tube having a proximal end and a distal end; and
a flexible printed circuit board assembly disposed in the flexible hollow tube, the flexible printed circuit board assembly defining part of at least one inspiratory passage within the flexible hollow tube and part of at least one expiratory passage within the flexible hollow tube, wherein the flexible printed circuit board assembly comprising:
at least one heating element configured to heat airflow within one or more of the at least one inspiratory passage and the at least one expiratory passage, and
at least one sensor configured to monitor a first property of the airflow within one or more of the at least one inspiratory passage and the at least one expiratory passage at multiple locations along an axial length of the flexible hollow tube.

2. The breathing circuit of claim 1, wherein the flexible printed circuit board assembly is disposed between an entirety of the axial length of the flexible hollow tube.

3. The breathing circuit of claim 1, wherein the flexible printed circuit board assembly is flat and has a dimension equal to an inner diameter of the flexible hollow tube.

4. The breathing circuit of claim 3, wherein the flexible printed circuit board assembly is disposed between two adjacent protrusions extending radially inward from an inner wall of the flexible hollow tube.

5. The breathing circuit of claim 1, wherein the flexible printed circuit board assembly defines part of one inspiratory passage within the flexible hollow tube and part of one expiratory passage within the flexible hollow tube.

6. The breathing circuit of claim 5, wherein the one inspiratory passage and the one expiratory passage are defined at opposite sides of the flexible printed circuit board assembly.

7. The breathing circuit of claim 1, wherein the flexible printed circuit board assembly has a generally circular cross section.

8. The breathing circuit of claim 7, wherein the flexible printed circuit board assembly is coaxial to the flexible hollow tube and shares a center axis with the flexible hollow tube.

9. The breathing circuit of claim 7, wherein the flexible printed circuit board assembly defines part of one inspiratory passage within the flexible hollow tube and part of two or more expiratory passages within the flexible hollow tube.

10. The breathing circuit of claim 1, wherein the flexible hollow tube is made of a material that is at least partially transparent.

11. The breathing circuit of claim 1, wherein the flexible printed circuit board assembly comprises one or more light emitting diodes that are configured to emit light if a predetermined condition of a monitored property of the airflow is detected.

12. The breathing circuit of claim 1, wherein the at least one sensor of the flexible printed circuit board assembly is configured to monitor a first property of the airflow within the at least one inspiratory passage and a second property of the airflow within the at least one expiratory passage.

13. The breathing circuit of claim 12, wherein the first property of the airflow within the at least one inspiratory passage and the second property of the airflow within the at least one expiratory passage are different types of properties.

14. The breathing circuit of claim 1, wherein the first property is temperature, humidity, pressure, airflow rate, presence of microbes or viruses, or concentration of a particular gas.

15. The breathing circuit of claim 1, wherein the flexible printed circuit board assembly comprises a wireless communications circuit to transmit values for the monitored first property.

\* \* \* \* \*